US011819710B2

(12) United States Patent
Kim et al.

(10) Patent No.: US 11,819,710 B2
(45) Date of Patent: Nov. 21, 2023

(54) METHOD, DEVICE, AND PROGRAM FOR CALCULATING BRACHYTHERAPY PLAN, AND BRACHYTHERAPY APPARATUS

(71) Applicants: THE ASAN FOUNDATION, Seoul (KR); UNIVERSITY OF ULSAN FOUNDATION FOR INDUSTRY COOPERATION, Ulsan (KR); NATIONAL CANCER CENTER, Goyang-si (KR); THE INDUSTRY & ACADEMIC COOPERATION IN CHUNGNAM NATIONAL UNIVERSITY, Daejeon (KR); KOREA INSTITUTE OF RADIOLOGICAL & MEDICAL SCIENCES, Seoul (KR)

(72) Inventors: Ho Jin Kim, Seoul (KR); Jung Won Kwak, Namyangju-si (KR); Byung Chul Cho, Anyang-si (KR); Sang Wook Lee, Seoul (KR); Chi Young Jeong, Seoul (KR); Young Kyung Lim, Paju-si (KR); Ui Jung Hwang, Goyang-si (KR); Sang Hyoun Choi, Namyangju-si (KR)

(73) Assignees: THE ASAN FOUNDATION, Seoul (KR); UNIVERSITY OF ULSAN FOUNDATION FOR INDUSTRY COOPERATION, Ulsan (KR); NATIONAL CANCER CENTER, Goyang-si (KR); THE INDUSTRY & ACADEMIC COOPERATION IN CHUNGNAM NATIONAL UNIVERSITY, Daejeon (KR); KOREA INSTITUTE OF RADIOLOGICAL & MEDICAL SCIENCES, Seoul (KR)

(*) Notice: Subject to any disclaimer, the term of this patent is extended or adjusted under 35 U.S.C. 154(b) by 508 days.

(21) Appl. No.: 17/110,957

(22) Filed: Dec. 3, 2020

(65) Prior Publication Data
US 2021/0085998 A1 Mar. 25, 2021

Related U.S. Application Data

(63) Continuation of application No. PCT/KR2019/006791, filed on Jun. 5, 2019.

(30) Foreign Application Priority Data

Jun. 5, 2018 (KR) .................. 10-2018-0065002

(51) Int. Cl.
*A61N 5/10* (2006.01)
*G06T 11/00* (2006.01)

(52) U.S. Cl.
CPC ......... *A61N 5/1031* (2013.01); *A61N 5/1001* (2013.01); *A61N 5/1064* (2013.01); *G06T 11/008* (2013.01); *A61N 2005/1034* (2013.01)

(58) Field of Classification Search
CPC ... A61N 5/1031; A61N 5/1001; A61N 5/1064
See application file for complete search history.

(56) References Cited

U.S. PATENT DOCUMENTS 6,260,005 B1   7/2001  Yang et al.
10,773,101 B2 * 9/2020  Otto ..................... H05K 999/99
(Continued)

FOREIGN PATENT DOCUMENTS

JP    2006-142043 A    6/2006
KR    10-2008-0044252 A   5/2008
(Continued)

OTHER PUBLICATIONS

John J. DeMarco et al., "A seed specific dose kernel method for low-energy brachytherapy dosimetry", Journal of Applied Clinical Medical Physics, vol. 4, No. 1, Winter 2003, (Received Aug. 5, 2002; accepted for publication Nov. 12, 2002) (Year: 2002).*
(Continued)

*Primary Examiner* — Hugh Maupin
(74) *Attorney, Agent, or Firm* — STUDEBAKER & BRACKETT PC; Sang Yoon Kang

(57) ABSTRACT

The present invention relates to a method, a device, and a program for calculating a brachytherapy plan, and a brachytherapy apparatus. The method comprises: a step in
(Continued)

which a computer obtains the number of radiation irradiation spots on the basis of radiation irradiation information (a radiation irradiation spot number obtaining step (S200)); a step in which the computer obtains target area information from a body model of a patient generated on the basis of medical image data of the patient (a target area information obtaining step (S400)); and a therapy plan calculating step (S600) in which the computer calculates, on the basis of the radiation irradiation information and the target area information, the radiation irradiation spots to which radiation is irradiated and the time length of irradiation to each radiation irradiation spot.

18 Claims, 11 Drawing Sheets

(56) References Cited

U.S. PATENT DOCUMENTS

| | | | |
|---|---|---|---|
| 2008/0091388 A1* | 4/2008 | Failla | A61N 5/1031 703/2 |
| 2012/0323599 A1* | 12/2012 | Bal | G16H 20/40 705/2 |
| 2013/0158879 A1* | 6/2013 | Hu | A61N 5/1031 702/19 |
| 2015/0367144 A1* | 12/2015 | Flynn | A61N 5/1031 600/7 |

FOREIGN PATENT DOCUMENTS

| | | |
|---|---|---|
| KR | 10-2013-0056624 A | 5/2013 |
| KR | 10-2017-0047214 A | 5/2017 |
| KR | 10-1794128 B1 | 11/2017 |
| WO | 2015/023307 A1 | 2/2015 |

OTHER PUBLICATIONS

International Search Report issued in PCT/KR2019/006791; dated Aug. 29, 2019.

An Office Action mailed by China National Intellectual Property Administration dated Jun. 13, 2022, which corresponds to Chinese Application No. 201980035876.0 and is related to U.S. Appl. No. 17/110,957.

* cited by examiner

FIG. 4
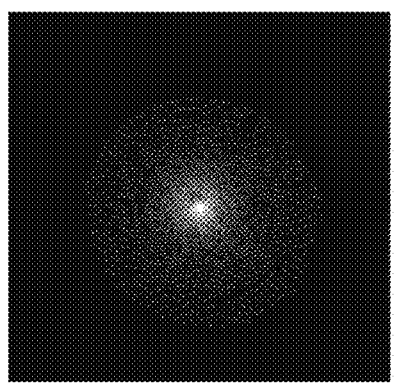
Dose of Monte Carlo calculations
[after rotating 60 degrees]
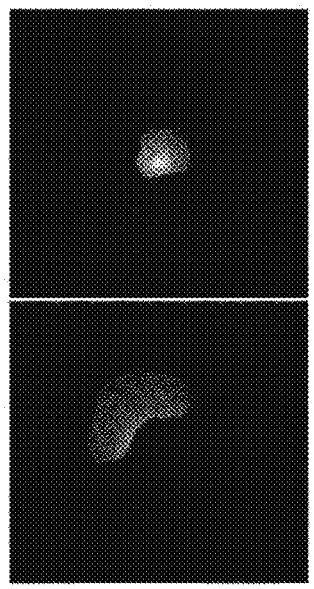
Extract target area portion
[after rotating 60 degrees]
Extract normal tissue [ex. bladder] portion
[after rotating 60 degrees]

FIG. 5

Divide target area and plurality of body areas, each of which has different characteristic, into separate group
[S610]

↓

Generate kernel matrix, which is m × n matrix, by setting number of radiation irradiation spots to column number n and setting number of voxels of specific group to row number m
[S620]

↓

Apply characteristic value of voxel included in each group to matrix value in kernel matrix depending to specific rule
[S640]

↓

Generate voxel dose matrix, which is m × 1 matrix, by applying dose value for each voxel to the same rule as kernel matrix to accomplish radiation therapy effect
[S660]

↓

Generate irradiation time length matrix, which is n × 1 matrix, for time length of irradiation to each radiation irradiation spot
[S670]

↓

Calculate combination of time lengths of irradiation to each radiation irradiation spot where multiplication of kernel matrix and irradiation time length matrix, which correspond to group, is approximated to voxel dose matrix for group
[S680]

FIG. 6

Generate kernel matrix, which is m × n matrix, by setting number of radiation irradiation spots to column number n and setting number of voxels of specific group to row number m
[S620]

↓

Apply characteristic value of voxel included in each group to matrix value in kernel matrix depending to specific rule
[S640]

↓

Generate voxel dose matrix, which is m × 1 matrix, by applying dose value for each voxel to the same rule as kernel matrix to accomplish radiation therapy effect
[S660]

↓

Generate irradiation time length matrix, which is n × 1 matrix, for time length of irradiation to each radiation irradiation spot
[S670]

↓

Calculate combination of time lengths of irradiation to each radiation irradiation spot where multiplication of kernel matrix and irradiation time length matrix, which correspond to group, is approximated to voxel dose matrix for group
[S680]

↓

Extract combination meeting condition where number of radiation irradiation spots becomes minimum and condition where dose for area except for target area becomes minimum, among combinations of time lengths of irradiation
[S690]

METHOD, DEVICE, AND PROGRAM FOR CALCULATING BRACHYTHERAPY PLAN, AND BRACHYTHERAPY APPARATUS

CROSS-REFERENCE TO RELATED APPLICATIONS

The present application is a continuation of International Patent Application No. PCT/KR2019/006791, filed on Jun. 5, 2019, which is based upon and claims the benefit of priority to Korean Patent Application No. 10-2018-0065002 filed on Jun. 5, 2018. The disclosures of the above-listed applications are hereby incorporated by reference herein in their entirety.

BACKGROUND

Embodiments of the inventive concept described herein relate to a method, a device, and a program for calculating a brachytherapy plan and a brachytherapy apparatus, and more particularly, relate to a method, a device, and a program for calculating a brachytherapy plan using a therapy tool inserted into the body to control a radiation irradiation location and a radiation irradiation direction and a brachytherapy apparatus including the same.

Radiation therapy for cancer patients may be roughly classified into two types. There are external beam radiation therapy of delivering radiation from a radiation source outside the body of a patient to a tumor and brachytherapy of delivering radiation from a radiation source inserted into the body of the patient.

In the brachytherapy therebetween, because the radiation source is inserted into the tumor to deliver a treatment dose to the tumor, a very high level of radiation is delivered to the tumor, but the amount of radiation delivered to a normal organ around the tumor may be considerably reduced.

In the brachytherapy, the radiation source is moved by means of a therapy tool inserted into the body to irradiate radiation. A technology capable of adjusting a radiation irradiation direction and adjusting three-dimensional (3D) radiation intensity is sufficiently developed in the therapy tool. Furthermore, there is a need to minimize a dose affecting normal tissues when brachytherapy is performed and there is a need to minimize a time taken to perform brachytherapy, but there is no method capable of resolving it.

SUMMARY

Embodiments of the inventive concept provide a method, a device, and a program for calculating a brachytherapy plan to minimize a change in location and angle of a radiation source to minimize the entire therapy time, while providing a target dose to a target area when inserting a therapy tool into the body and performing brachytherapy and a brachytherapy apparatus.

The technical problems to be solved by the inventive concept are not limited to the aforementioned problems, and any other technical problems not mentioned herein will be clearly understood from the following description by those skilled in the art to which the inventive concept pertains.

According to an exemplary embodiment, a method for calculating a brachytherapy plan may include obtaining, by a computer, the number of radiation irradiation spots based on radiation irradiation information, the radiation irradiation information including the number of locations capable of arranging radiation sources and an angle change unit and the radiation irradiation spot being a specific angle direction at a specific source location, obtaining, by the computer, target area information from a patient body model generated based on medical image data of a patient, the target area information including arrangement information on a voxel space included in a target area, and calculating, by the computer, radiation irradiation spots to which radiation is irradiated and a time length of irradiation to each of the radiation irradiation spots, based on the radiation irradiation information and the target area information.

Furthermore, as another embodiment, the calculating may include calculating a combination of time lengths of irradiation to radiation irradiation spots, the number of which becomes minimum, among combinations of time lengths of irradiation to a plurality of radiation irradiation spots for the target area.

Furthermore, as another embodiment, the calculating may include calculating the time length of irradiation to the radiation irradiation spot by applying the result, calculated by applying a dose distribution obtained when applying radiation intensity to be applied to rear therapy in water in a specific direction to the Monte Carlo simulation method, to each radiation irradiation spot in the patient body model.

Furthermore, as another embodiment, the method may further include moving a radiation irradiation location along a straight line in the direction of a specific axis. The calculating may include correcting and applying the result of Monte Carlo calculations depending on information tilted in the direction of the axis.

Furthermore, as another embodiment, the calculating may include generating a kernel matrix, which is an m×n matrix, by setting the number of the radiation irradiation spots to a column number n and setting the number of voxels of a specific group to a row number m, applying a characteristic value of a voxel included in each group to a matrix value in the kernel matrix depending on a specific rule, generating a voxel dose matrix, which is an m×1 matrix, by applying a dose value for each voxel to the same voxel order assignment rule as the kernel matrix to accomplish a radiation therapy effect, generating an irradiation time length matrix, which is an n×1 matrix, for a time length of irradiation to each radiation irradiation spot, and calculating a combination of time lengths of irradiation to each radiation irradiation spot where multiplication of the kernel matrix and the irradiation time length matrix, which correspond to the group, is approximated to the voxel dose matrix for the group.

Furthermore, as another embodiment, the method may further include dividing the target area and a plurality of body areas, each of which has a different characteristic, into a separate group.

Furthermore, as another embodiment, the generating of the kernel matrix may include generating a separate kernel matrix for each separate group. The calculating of the combination of the time lengths of irradiation may include calculating a radiation irradiation length combination meeting the separate kernel matrix for each separate group and the voxel dose matrix. The separate kernel matrix may have the same column number by applying the same radiation irradiation spot condition.

Furthermore, as another embodiment, the calculating may further include extracting a combination meeting a condition where the number of radiation irradiation spots becomes minimum and a condition where a dose for an area except for the target area becomes minimum, among combinations of time lengths of irradiation.

Furthermore, as another embodiment, the condition where the number of the radiation irradiation spots becomes minimum may include a condition where a value obtained by applying an $L_0$-norm algorithm becomes minimum, among the combinations of the time lengths of irradiation.

Furthermore, as another embodiment, the condition where the dose for the area except for the target area becomes minimum may include a condition where a value obtained by applying an $L_2$-norm algorithm to a difference between multiplication of the separate kernel matrix and the irradiation time length matrix for the group and an ideal voxel dose matrix for each group becomes minimum.

According to an exemplary embodiment, a program for calculating a brachytherapy plan may be combined with hardware and may be stored in a medium to execute the method for calculating the brachytherapy plan.

According to an exemplary embodiment, a device for calculating a brachytherapy plan may include a radiation irradiation spot number obtaining unit that obtains the number of radiation irradiation spots based on radiation irradiation information, a target area information obtaining unit that obtains target area information from a patient body model generated based on medical image data of a patient, and a therapy plan calculating unit that calculates radiation irradiation spots to which radiation is irradiated and a time length of irradiation to each of the radiation irradiation spots, based on the radiation irradiation information and the target area information. The radiation irradiation information may include the number of locations capable of arranging radiation sources and an angle change unit. The radiation irradiation spot may be a specific angle direction at a specific source location. The target area information may include arrangement information on a voxel space included in a target area.

Furthermore, as another embodiment, the therapy plan calculating unit may calculate a combination of time lengths of irradiation to radiation irradiation spots, the number of which becomes minimum.

Furthermore, as another embodiment, the therapy plan calculating unit may divide the target area and a plurality of body areas respectively corresponding to body tissues into a separate group in the patient body model, may generate a separate kernel matrix by setting the number of the radiation irradiation spots to a column number n and setting the number of voxels of a specific group to a row number m, may apply a characteristic value of a voxel included in each group to a matrix value in the separate kernel matrix depending on a specific rule, may generate a voxel dose matrix, which is an m×1 matrix, by applying a dose value for each voxel to the same voxel order assignment rule as the kernel matrix to accomplish a radiation therapy effect, may generate an irradiation time length matrix, which is an n×1 matrix, for a time length of irradiation to each radiation irradiation spot, and may calculate a combination of time lengths of irradiation to each radiation irradiation spot where multiplication of the separate kernel matrix and the irradiation time length matrix, which correspond to each group, is approximated to the voxel dose matrix for each group. The separate kernel matrix may have the same column number by applying the same radiation irradiation spot condition.

Furthermore, as another embodiment, the therapy plan calculating unit may extract a combination meeting a condition where the number of radiation irradiation spots becomes minimum and a condition where a dose for an area except for the target area becomes minimum, among combinations of time lengths of irradiation.

According to an exemplary embodiment, a brachytherapy apparatus may include a therapy tool that is inserted into the body to control a radiation irradiation direction and radiation intensity and a control means that obtains the number of radiation irradiation spots based on radiation irradiation information, obtains target area information from a patient body model generated based on medical image data of a patient, calculates radiation irradiation spots to which radiation is irradiated and a combination of time lengths of irradiation to each of the radiation irradiation spots, based on the radiation irradiation information and the target area information, calculates a combination of time lengths of irradiation to radiation irradiation spots, the number of which becomes minimum, and radiation irradiation spots being where a dose irradiated to a normal tissue becomes minimum. The radiation irradiation information may include the number of locations capable of arranging radiation sources and an angle change unit. The radiation irradiation spot may be a specific angle direction at a specific source location. The target area information may include arrangement information on a voxel space included in a target area.

BRIEF DESCRIPTION OF THE FIGURES

The above and other objects and features will become apparent from the following description with reference to the following figures, wherein like reference numerals refer to like parts throughout the various figures unless otherwise specified, and wherein:

FIG. 4 is a drawing illustrating a process of extracting a portion corresponding to each body area in an ideal dose distribution according to an embodiment of the inventive concept;

FIG. 5 is a flowchart illustrating a process of generating a kernel matrix for each target area and every a plurality of body areas and calculating a therapy plan based on a matrix according to an embodiment of the inventive concept;

FIG. 6 is a flowchart illustrating a process of calculating a therapy plan, which further includes a process of calculating a combination of time lengths of irradiation in an optimal condition, according to an embodiment of the inventive concept;

DETAILED DESCRIPTION

Figure 1:
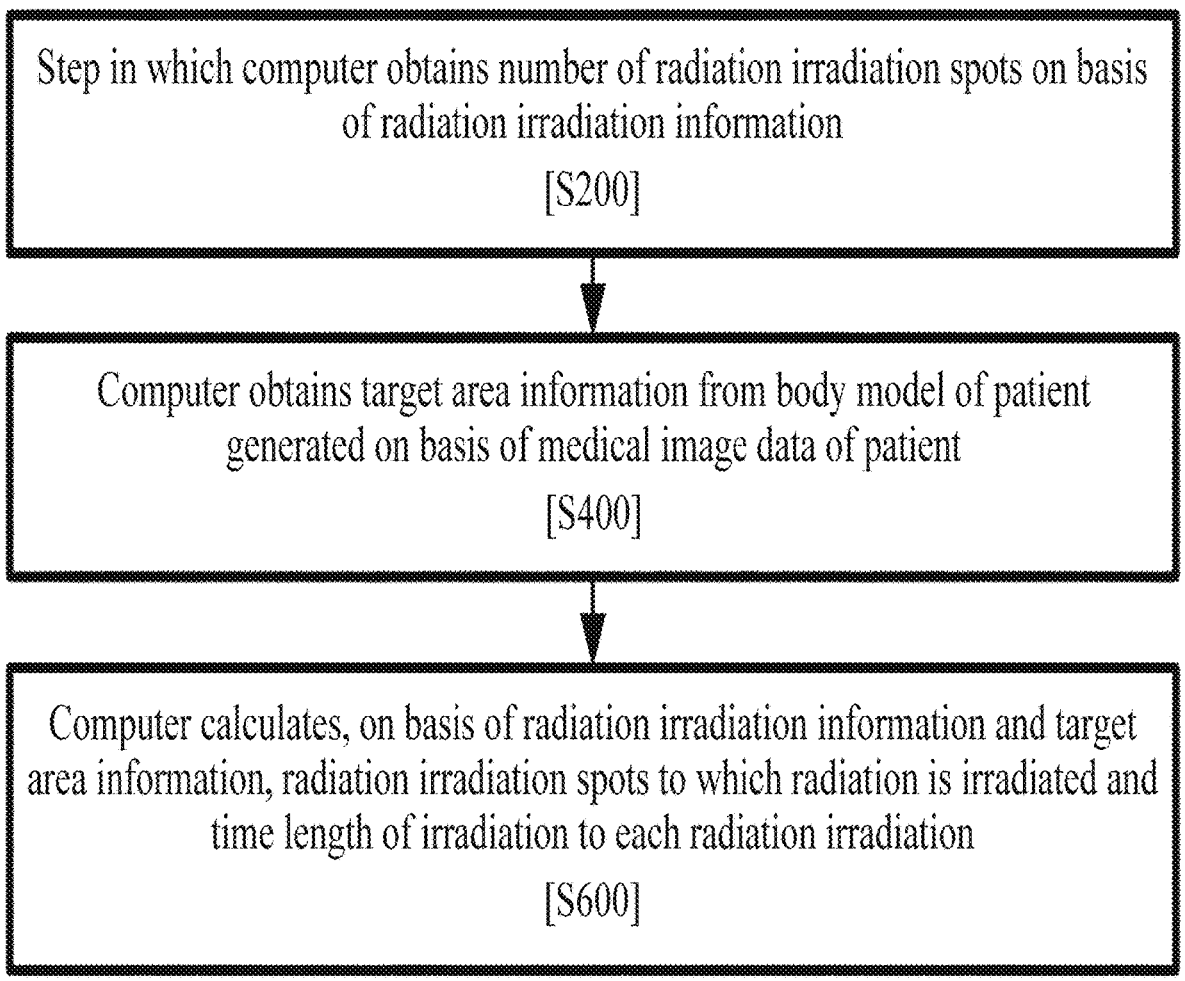
FIG. 1 is a flowchart illustrating a method for calculating a brachytherapy plan according to an embodiment of the inventive concept.

Hereinafter, an embodiment of the inventive concept will be described in detail with reference to the accompanying drawings. Advantages, features, and methods of accomplishing the same will become apparent with reference to embodiments described in detail below together with the accompanying drawings. However, the inventive concept is not limited by embodiments disclosed hereinafter, and may be implemented in various forms. Rather, these embodiments are provided to so that this disclosure will be through and complete and will fully convey the concept of the invention to those skilled in the art, and the inventive concept will only be defined by the appended claims. The same reference denotations refer to the same components throughout the specification.

Unless otherwise defined herein, all terms (including technical and scientific terms) used in the specification may have the same meaning that is generally understood by a person skilled in the art. Also, terms which are defined in a dictionary and commonly used should be interpreted as not in an idealized or overly formal detect unless expressly so defined.

Terms used in the specification are used to describe embodiments of the inventive concept and are not intended to limit the scope of the inventive concept. In the specification, the terms of a singular form may include plural forms unless otherwise specified. The expressions "comprise" and/or "comprising" used herein indicate existence of one or more other elements other than stated elements but do not exclude presence of additional elements.

The "brachytherapy tool" in the specification may include all of therapy tools used for brachytherapy performed after a radiation source is inserted into the body. Particularly, the "brachytherapy tool" may include a tool capable of controlling both of a location where radiation is irradiated and a direction where radiation is irradiated. Furthermore, the "therapy tool" may have a thin, long shape, a curved shape, or the like because it may be formed in various shapes.

The "computer" in the specification may include all of various devices which perform operation processing. For example, the computer may correspond to a smartphone, a tablet personal computer (PC), a cellular phone, a personal communication service (PCS) phone, a synchronous/asynchronous international mobile telecommunication-2000 (IMT-2000) mobile phone, a palm PC, a personal digital assistant (PDA), or the like as well as a desktop PC or a note book. Furthermore, the computer may correspond to medical equipment which obtains or observes a medical image. Furthermore, the computer may correspond to a server computer connected with various client computers.

The "medical image data" in the specification may refer to an image obtained by a medical imaging device. The "medical image data" may include magnetic resonance imaging, computed tomography imaging, or the like.

The "target area" in the specification may refer to an object area to be treated through radiation irradiation. For example, the "target area" may correspond to a tumor area to which radiation should be irradiated.

In the specification, the "separate group" may refer to a voxel group divided for each target area or each body tissue.

Hereinafter, a description will be given of a method, a device, and a program for calculating a brachytherapy plan and a brachytherapy apparatus according to embodiments of the inventive concept.

Figure 2A:
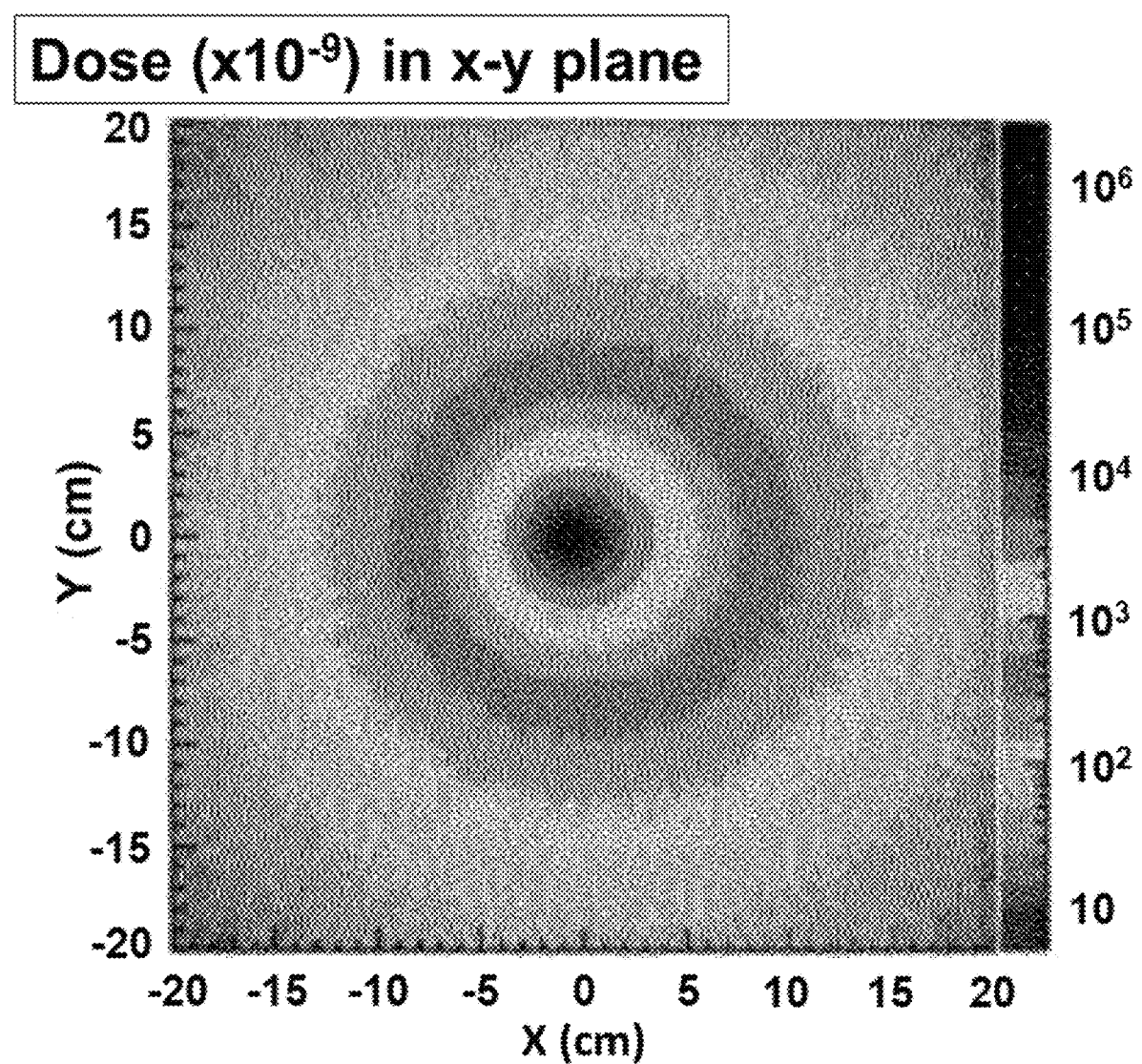
FIGS. 2A to 2C are drawings illustrating a dose distribution in an ideal condition according to an embodiment of the inventive concept.
Figure 2B:
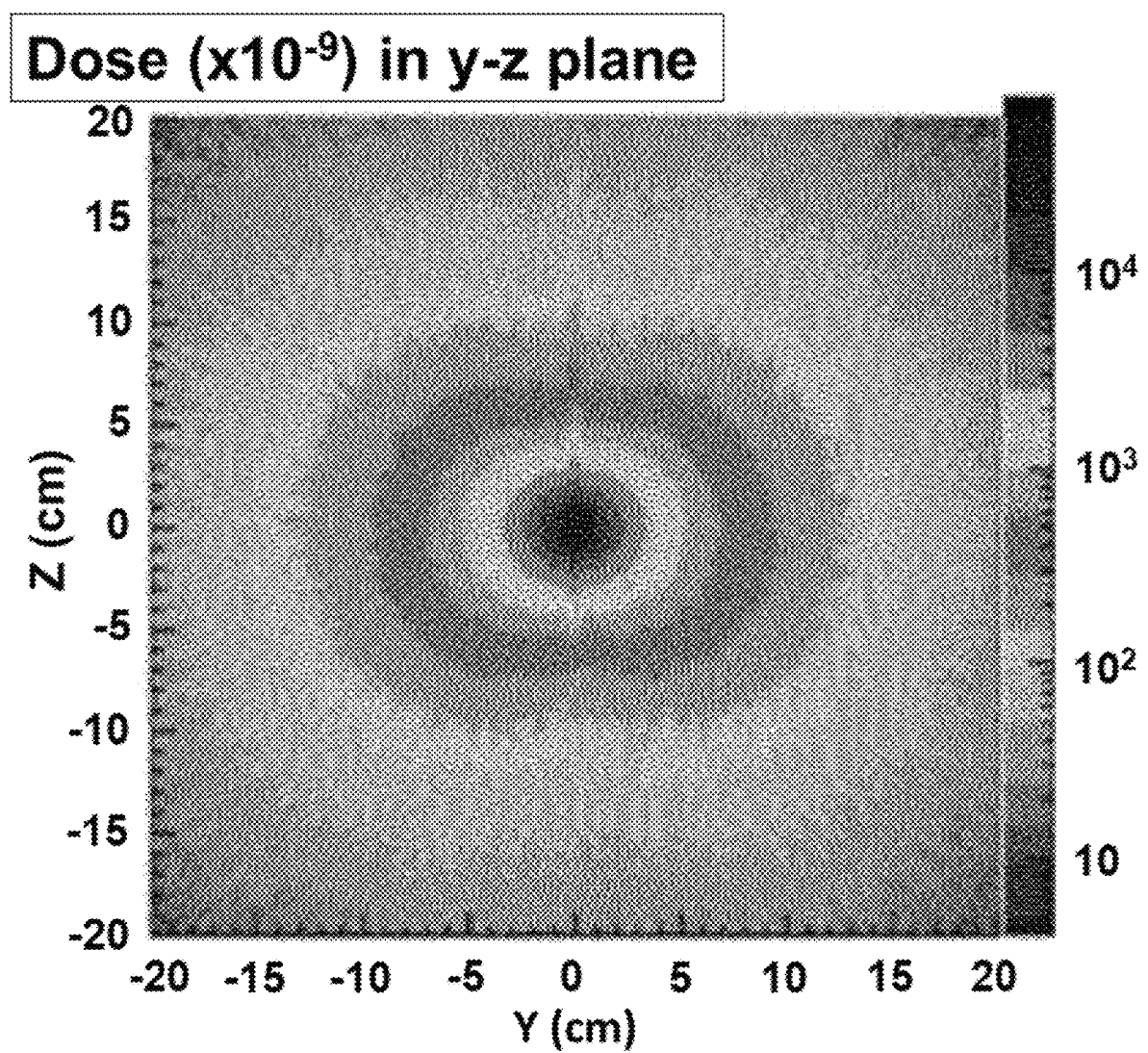
Figure 2C:
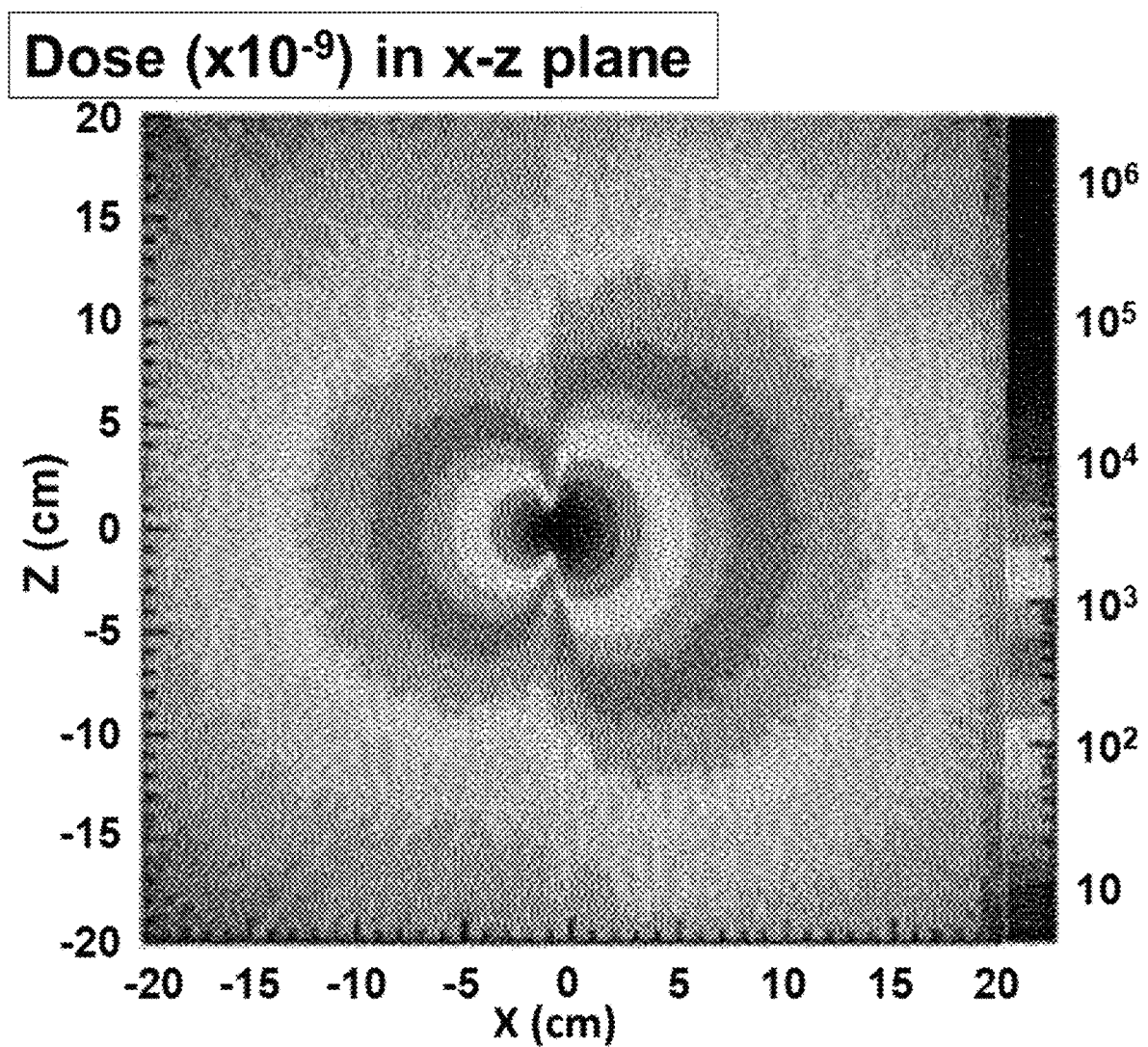

FIG. 1 is a flowchart illustrating a method for calculating a brachytherapy plan according to an embodiment of the inventive concept. FIGS. 2A to 2C are drawings illustrating a dose distribution in an ideal condition according to an embodiment of the inventive concept.

Referring to FIG. 1, the method for calculating the brachytherapy plan according to an embodiment of the inventive concept may include obtaining (S200), by a computer, the number of radiation irradiation spots based on radiation irradiation information, obtaining (S400), by the computer, target area information from a patient body model generated based on medical image data of the patient, and calculating (S600), by the computer, a radiation irradiation spot to which radiation is irradiated and a time length of radiation to each radiation irradiation spot. Hereinafter, each operation will be described in detail.

In operation S200, the computer may obtain the number of radiation irradiation spots based on radiation irradiation information. The radiation irradiation information may include the number of locations capable of arranging radiation sources of a brachytherapy tool and an angle change unit.

The brachytherapy tool may have various forms capable of changing a radiation irradiation location and a radiation irradiation direction. As an embodiment, the brachytherapy tool may move the radiation irradiation location along a straight line in the direction of a specific axis. In other words, the brachytherapy tool may be overall formed in thin, long shape. Furthermore, as another embodiment, the brachytherapy tool may have a curved shape to be inserted into a bent body part. For example, because a therapy tool in a shape curved to suit a body structure should be used to irradiate radiation to a tumor of the same location as uterine cancer, the brachytherapy tool may be formed in a structure bent at a specific location or a structure where a first structure and a second structure are connected at a specific angle.

As an embodiment, the brachytherapy tool where an area irradiating radiation is thin and long may be disposed on a specific axis in the body of a patient. The computer may obtain radiation irradiation information for performing a therapy plan on the assumption that the brachytherapy tool is disposed on an axis to be actually disposed in a therapy situation. For example, when radiation is irradiated to a tumor in the uterus of a uterine cancer patient, the computer may arrange the brachytherapy tool to be parallel to the z-axis direction. The computer may rotate and correct a patient body model in advance such that the brachytherapy tool is disposed in the center of a tube in the body when the brachytherapy tool is disposed parallel to the z-axis.

Furthermore, the brachytherapy tool may have a radiation source disposed at each irradiation location of an internal space extended in a longitudinal direction to irradiate radiation to a target area needing therapy. The radiation source may be connected to an end of a thin, long wire provided in the external brachytherapy tool to irradiate radiation. In other words, the radiation source may be located in a receiving space formed in the thin, long shape of the brachytherapy tool.

Furthermore, the brachytherapy tool may be formed in a structure capable of adjusting a direction where radiation may be exposed to the outside. The brachytherapy tool may change a radiation irradiation direction as a user rotates an operating part or a driving part in the outside.

In detail, when performing therapy while changing a radiation irradiation location and a radiation irradiation direction, the computer may set a location (i.e., the radiation irradiation location) to which radiation should be irradiated, in the brachytherapy tool of the thin, long shape. For example, the computer may divide the entire section, to which radiation may be irradiated, at equal intervals and may set a plurality of radiation irradiation locations. When brachytherapy is performed for the treatment of uterine cancer, the computer may set a radiation irradiation location at intervals of 2.5 mm in the brachytherapy tool disposed in a uterine area of a patient. Thereafter, the computer may divide an angle range in which the brachytherapy tool is rotatable in specific reference units to set the number of radiation irradiation directions. For example, when the brachytherapy tool is rotatable 360 degrees, the computer may divide 360 degrees by an angle (e.g., 30 degrees), which is a specific reference unit, in a reference direction (e.g., a right direction of the body of a patient) to set 12 irradiation directions. As a result, the computer may set all the radiation irradiation spots using the set radiation irradiation locations and the set radiation irradiation directions. The radiation irradiation spot may be a radiation irradiation condition in which a radiation irradiation location condition and a radiation irradiation direction condition are combined (i.e., information about a specific angle direction at a location where a specific radiation source is disposed). Furthermore, the computer may calculate the number of all of radiation irradiation spots using the number of the radiation irradiation locations and the number of the radiation irradiation directions.

In operation S400, the computer may obtain target area information from a patient body model generated based on medical image data of the patient. The patient body model may be generated based on various medical image data. As an embodiment, when computed tomography (CT) image data is used as medical image data, the computer may identify a body density distribution using a specific Hounsfield unit value to generate the patient body model. In other words, the patient body model may be three-dimensional (3D) patient body data generated based on specific medical image data.

The computer may extract a target area from the patient body model to obtain the target area information. The target area may be an area where radiation therapy should be performed in the body of the patient, which correspond to a tumor area. The target area information may include arrangement information on a voxel space included in the target area. For example, the target area information may include the number of voxels included in the target area, a location value (e.g., a vector value from a reference location), or the like.

Furthermore, as another embodiment, the computer may obtain information about a plurality of body portions from the patient body model. Because radiation has an influence on a normal body portion which is on a path from the brachytherapy tool to the target area or around the target area in the process of performing radiation therapy for the target area using brachytherapy, the computer may extract a plurality of normal body areas to generate normal body area information. In this case, because there is a difference in characteristic (i.e., body density) for radiation per body portion, the computer may separate a different body portion from the plurality of normal body areas.

Furthermore, as an embodiment, as will be described below, the computer may set the extracted target area and the plurality of normal body areas to a separate group and may calculate a brachytherapy plan (e.g., provide a desired dose to the target area and provide a minimum dose to the normal body areas).

In operation S600, the computer may calculate radiation irradiation spots to which radiation is irradiated and a time length of irradiation to each of the radiation irradiation spots, based on the radiation irradiation information and the target area information. The computer may extract one or more radiation irradiation spots which minimize a dose affecting a normal tissue while providing the dose to the target area. In other words, the computer may calculate a radiation irradiation location and direction capable of providing a dose to the target area while allowing the dose to have a little influence on a normal tissue. Because it is unable to adjust the intensity itself of the radiation source after the radiation source is inserted into the body, the computer may adjust a time taken for radiation to be irradiated to a specific radiation irradiation spot using the inserted radiation source, which irradiates a specific intensity of radiation, to adjust a dose provided to the inside of the body.

The computer may calculate several combinations of time lengths of irradiation, which are capable of performing brachytherapy to suit target area information. When calculating a therapy plan using the target area information and the normal body area information, the compute may calculate several combinations of time lengths of irradiation. The user may select one of the several combinations of time lengths of irradiation to apply the selected combination to real brachytherapy. The computer may provide a specific combination of time lengths of irradiation, which is capable of minimizing a dose provided to a normal tissue and minimizing a therapy time length, to perform therapy using the specific combination.

Furthermore, as another embodiment, in operation S600, the computer may calculate a combination of time lengths of irradiation to radiation irradiation spots, the number of which becomes minimum, among combinations of time lengths of irradiation to a plurality of radiation irradiation spots for the target area. In detail, when there is an increase in the process where a medical team unloads a radiation source to adjust radiation intensity itself, adjusts radiation intensity, and inserts the radiation source into the body again, the entire time taken to perform brachytherapy may become longer. In other words, as the process of inserting a radioactive substance into a tool is more repeated, a time taken to perform therapy may become longer. Furthermore, when there is an increase in moved radiation irradiation spot although one radiation source is used, there may be an increase in time taken in the process of changing radiation irradiation spots, such that the entire therapy time becomes longer. Furthermore, when there is an increase in radiation irradiation spot, there may be an increase in probability that radiation will be exposed to the inside of the patient in the process of moving the radiation source. Thus, when the number of times of unloading the radiation source to the outside is minimized and when the number of times of changing the radiation irradiation spot is reduced, the entire time when brachytherapy is performed may become shorter. To this end, the computer may apply a manner which adjusts a length of time taken to irradiate radiation in a corresponding direction at a specific radiation irradiation spot in a state where the intensity itself of radiation is the same and may discover a condition where the number of radiation irradiation spots becomes minimum.

Furthermore, various manners are applicable to a manner which calculates a combination of time lengths of irradiation to one or more radiation irradiation spots. As an embodiment, in operation S600, the computer may apply the result of Monte Carlo calculations in which radiation is irradiated in a specific direction in an ideal condition (e.g., a condition where radiation is irradiated in a cube-shaped water tank with water) to each radiation irradiation point in the patient body model to calculate the time length of irradiation. In other words, the computer may apply the result, calculated by applying a dose distribution obtained when applying radiation intensity to be applied to rear therapy in water in a specific direction to the Monte Carlo simulation method, to each radiation irradiation spot in the patient body model to calculate a time length of irradiation to the radiation irradiation spot. As shown in FIGS. 2A to 2C, the result of Monte Carlo calculations may be a dose distribution result obtained when a radiation intensity condition to be applied to real therapy in water is applied in a specified direction. Because most of the human body is made up of water, as the ideal result of Monte Carlo calculations applied to the water is applied to each radiation irradiation spot, the computer may extract one or more irradiation spots to which radiation should be irradiated and may calculate a time length of irradiation to each irradiation spot for providing a desired dose to the target area.

Furthermore, as another embodiment, in operation S600, the computer may correct and apply the result of Monte Carlo calculations depending on information tilted in the direction of the axis. An arrangement direction in which the result of Monte Carlo calculations is obtained based on a state where body organs are arranged may fail to be matched with a direction in which radiation is irradiated upon therapy. Thus, the computer may correct an ideal radiation dose distribution image or a patient body model to match the direction of an axis where a brachytherapy tool is disposed when performing Monte Carlo calculations with the direction of an axis where the brachytherapy tool is disposed upon real therapy. In detail, when the brachytherapy tool is inserted into a specific tube-shaped body portion, the computer may rotate the ideal radiation dose distribution image or the patient body model to match an axis parallel to a central axis of the tube-shaped body portion with an axis where the brachytherapy tool is placed upon Monte Carlo calculations.

Figure 3:
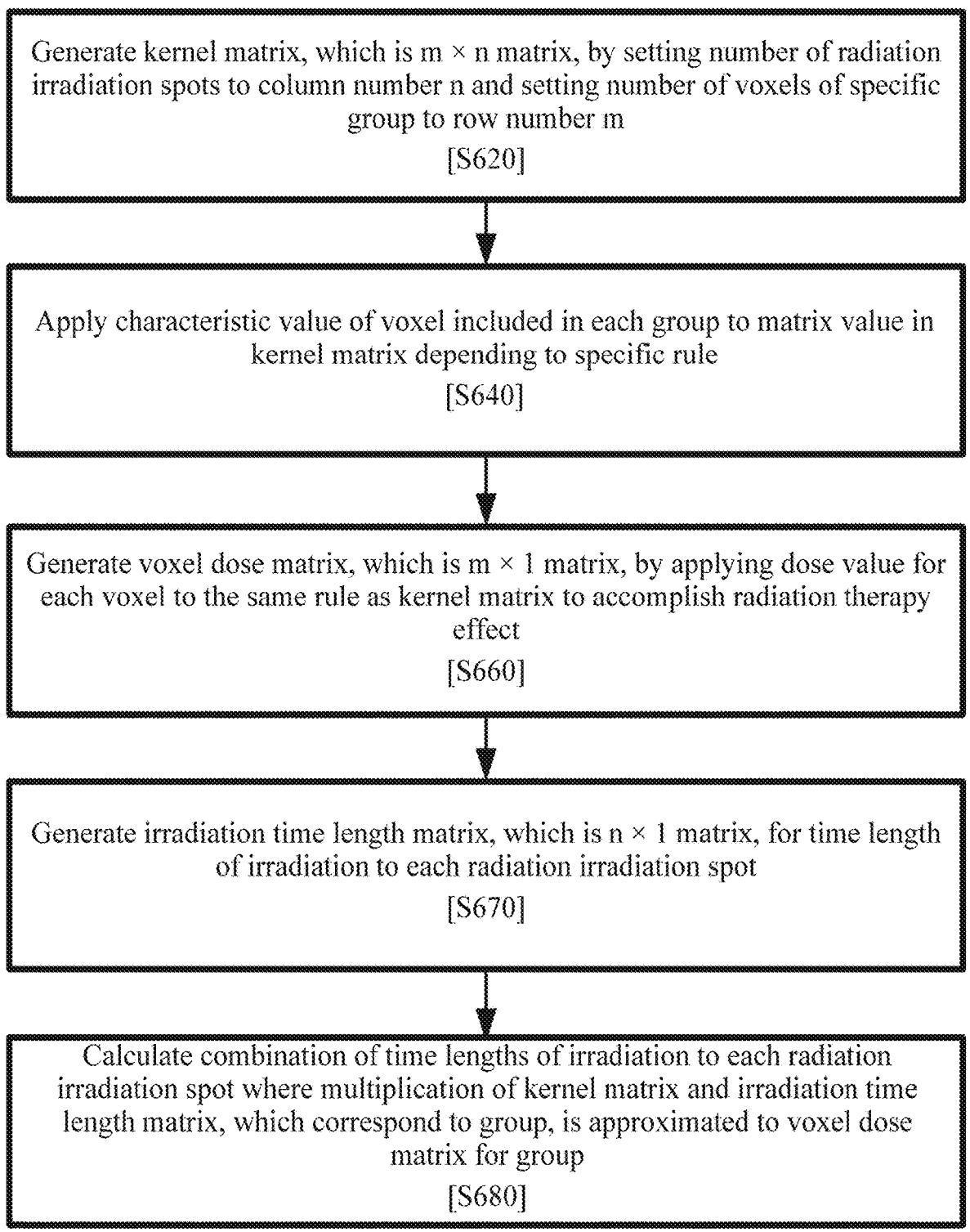
FIG. 3 is a flowchart illustrating a process of calculating a therapy plan based on a matrix according to an embodiment of the inventive concept.
Figure 7:
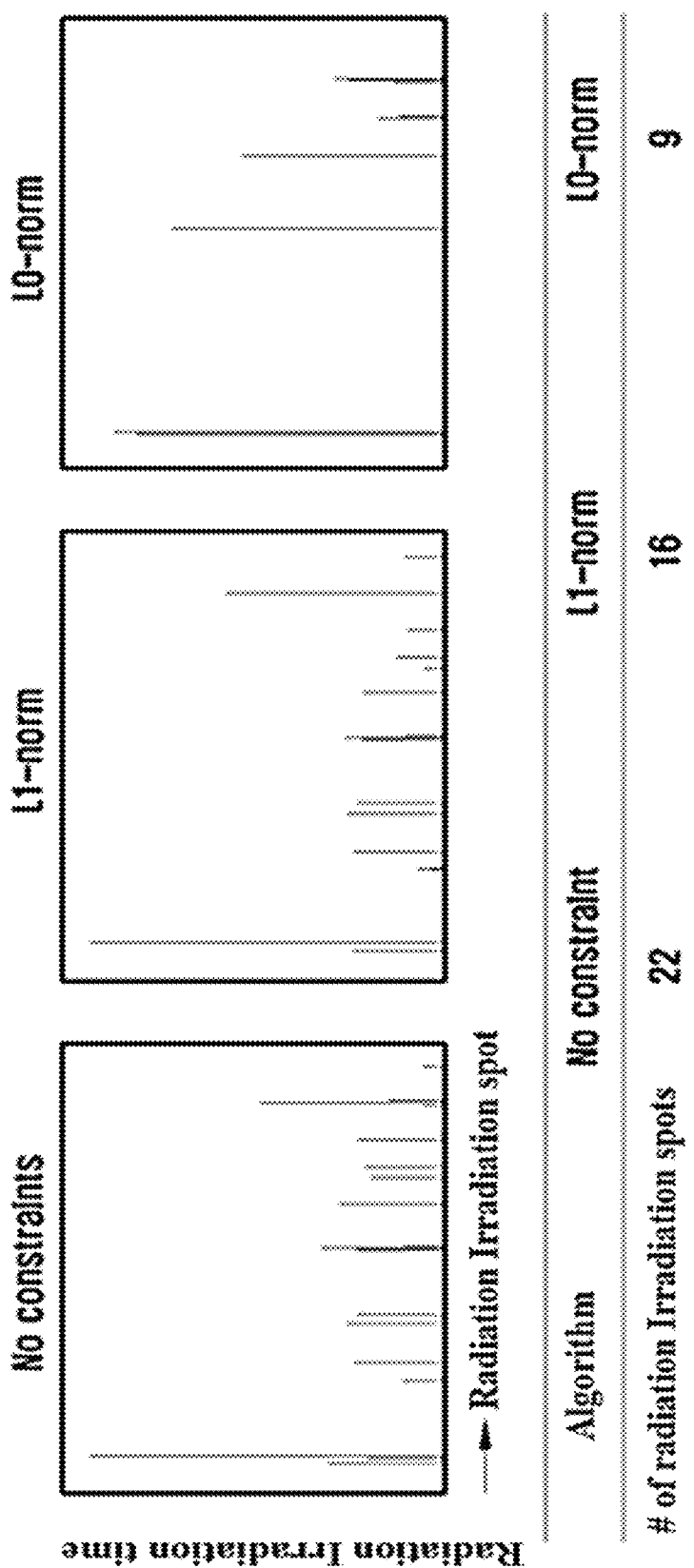
FIG. 7 is a drawing illustrating an example of comparing the number of times of radiation irradiation and a total time length where radiation is irradiated, i) when not applying an $L_k$-norm algorithm to a combination of time lengths of irradiation, ii) when applying an $L_1$-norm algorithm to the combination of time lengths of irradiation, and iii) when applying an $L_0$-normal algorithm to the combination of time lengths of irradiation, according to an embodiment of the inventive concept.

Furthermore, as another embodiment, in operation S600, the computer may perform a process of calculating a combination of time lengths of irradiation using a matrix. Hereinafter, the process of calculating the therapy plan based on the matrix will be described in detail. FIG. 3 is a flowchart illustrating a process of calculating a therapy plan based on a matrix according to an embodiment of the inventive concept. FIG. 4 is a drawing illustrating a process of extracting a portion corresponding to each body area in an ideal dose distribution according to an embodiment of the inventive concept. FIG. 5 is a flowchart illustrating a process of generating a kernel matrix for each target area and every a plurality of body areas and calculating a therapy plan based on a matrix according to an embodiment of the inventive concept. FIG. 6 is a flowchart illustrating a process of calculating a therapy plan, which further includes a process of calculating a combination of time lengths of irradiation in an optimal condition, according to an embodiment of the inventive concept. FIG. 7 is a drawing illustrating an example of comparing the number of times of radiation irradiation and a total time length where radiation is irradiated, i) when not applying an $L_k$-norm algorithm to a combination of time lengths of irradiation, ii) when applying an $L_1$-norm algorithm to the combination of time lengths of irradiation, and iii) when applying an $L_0$-normal algorithm to the combination of time lengths of irradiation, according to an embodiment of the inventive concept.

As an embodiment, as shown in FIG. 3, the process of calculating the therapy plan based on the matrix may include generating (S620) a kernel matrix, which is an m×n matrix, by setting the number of radiation irradiation spots to a column number n and setting the number of voxels of a specific group to a row number m, applying (S640) a characteristic value of a voxel included in each group to a matrix value in the kernel matrix depending on a specific rule, generating (S660) a voxel dose matrix, which is an m×1 matrix, by applying the same voxel order assignment rule as the kernel matrix to a dose value for each voxel to accomplish a radiation therapy effect, generating (S670) a radiation time length matrix, which is an n×1 matrix, for a time length of radiation to each radiation irradiation spot, and calculating (S680) a combination of time lengths of radiation to each radiation irradiation spot where multiplication of the kernel matrix and the irradiation time length matrix, which correspond to the group, is approximated to the voxel dose matrix for the group.

First of all, in operation S620, a computer may set the number of radiation irradiation spots to a column number n (where n is a natural number) and may set the number of voxels of a specific group to a row number m (where m is a natural number) to generate a kernel matrix which is an m×n matrix. The computer may determine an order where n radiation irradiation spots are matched to each column and may determine an order where m voxels in the specific group are matched to each row. As described above, n corresponding to the number of the radiation irradiation spots may be calculated by multiplying the number of radiation irradiation locations by the number of radiation irradiation directions. For example, when the 12 radiation irradiation locations are used and when 24 radiation irradiation directions obtained by dividing 360 degrees at intervals of 15 degrees which is a unit angle are used, n is 288.

In operation S640, the computer may apply a characteristic value of a voxel included in each group to a matrix value in the kernel matrix depending on a specific rule. The character value of the voxel may be a dose value provided to the voxel during a unit time when the result of Monte Carlo calculations is applied to a specific radiation irradiation spot. As shown in FIG. 4, the computer may apply an ideal dose distribution (e.g., a dose distribution obtained when applying radiation intensity to be applied to real therapy in water in a specific direction) to the specific radiation irradiation spot to extract a target area portion and may obtain a dose value for each voxel to apply the obtained dose value to a characteristic value of the voxel.

In operation S660, the computer may apply a dose value for each voxel to the same voxel order assignment rule as the kernel matrix to accomplish a radiation therapy effect, thus generating a voxel dose matrix which is an m×1 matrix. The voxel order assignment rule may be to determine a voxel order assigned to each row. In other words, the computer may apply the same matching order as being applied to each row in the kernel matrix to the voxel dose matrix. The matrix value in the voxel dose matrix may be a total dose (i.e., a target dose) which should be irradiated to each voxel to accomplish radiation therapy.

In operation 670, the computer may generate an irradiation time length matrix, which is an n×1 matrix, for a time length of irradiation to each radiation irradiation spot. In other words, the computer may generate a matrix which uses a value of a dwelling time while irradiating radiation to each radiation irradiation spot as a variable. The computer may apply the same radiation irradiation spot order as being applied to the kernel matrix to the irradiation time length matrix.

In operation S680, the computer may calculate a combination of time lengths of irradiation to each radiation irradiation spot where multiplication of the kernel matrix and the irradiation time length matrix, which correspond to the group, is approximated to the voxel dose matrix for the group. The combination of the time lengths of irradiation may include information (i.e., a location and a direction) of a radiation irradiation spot to which radiation should be irradiated and information about a time length of irradiation to the radiation irradiation spot. In detail, because the combination of the time lengths of irradiation is a calculation value of an irradiation time length matrix calculated through matrix formula calculation, the computer may identify information about a radiation irradiation spot using a column number indicated by a matrix value which is not "0" and may identify a time length of irradiation to the radiation irradiation spot using the matrix value itself. When a plurality of variables are included in the irradiation time length matrix depending on including a plurality of radiation irradiation spots upon brachytherapy, the computer may calculate several combinations of time lengths of irradiation, which meet the matrix formula.

Furthermore, as another embodiment, as shown in FIG. 5, operation S600 according to an embodiment of the inventive concept may further include dividing (S610) a target area and a plurality of body areas, each of which has a different characteristic, into a separate group. In other words, when a plurality of normal body areas influenced upon brachytherapy and the target area which should be treated have different density characteristics, the computer may divide the plurality of body areas into the separate group.

After dividing the plurality of normal body areas and the target area into the separate group, in operation S620, the computer may generate a separate kernel matrix for each separate group. Thereafter, in operation 680, the computer may calculate a combination of irradiation lengths of radiation, which meets the separate kernel matrix for each separate group and the voxel dose matrix. The separate kernel matrix may have the same column number by applying the same radiation irradiation spot condition. The computer may apply the same radiation irradiation spot condition to the kernel matrix and the irradiation time length matrix and may add an irradiation time length matrix calculated using each separate kernel matrix and the voxel dose matrix to calculate a final time of irradiation to each radiation irradiation spot. Furthermore, because the separate kernel matrix is calculated for a different area (i.e., a normal body area or a target area), it may have an m value which varies with the number of voxels included in the area.

Furthermore, as another embodiment, as shown in FIG. 6, operation S600 may further include extracting (S690) a combination meeting a condition where the number of radiation irradiation spots becomes minimum and a condition with a dose for an area except for the target area becomes minimum, among combinations of time lengths of irradiation. In other words, the computer may calculate a combination of time lengths of irradiation for accomplishing a desired radiation therapy effect, minimizing damage for a normal area, and minimizing a therapy time. In detail, as described above, the computer may discover the condition where the number of the radiation irradiation spots becomes minimum and may calculate a combination of time lengths of irradiation where the radiation therapy time is minimized. Furthermore, the computer may calculate a condition, which is close to a desired target dose for the target area, in which a dose close to "0" affects another normal body area, and may calculate a combination of time lengths of irradiation, which meets a condition where the dose for an area except for the target area becomes minimum.

As an embodiment, the computer may calculate i) a condition where the number of radiation irradiation spots becomes minimum and ii) a condition where the dose for the area except for the target area becomes minimum, using matrix calculation.

The condition where the number of the radiation irradiation spots becomes minimum may be discovered by applying an $L_k$-norm algorithm (where k is a real number which is greater than or equal to "0" or is less than or equal to "1") to the irradiation time length matrix. As an embodiment, the condition where the number of the radiation irradiation spots becomes minimum may include a condition where a value to which an L0-norm algorithm is applied becomes minimum, among a plurality of combinations of time lengths of irradiation. The $L_0$-norm algorithm may be to process and add a matrix value, which is not "0" in a specific matrix, as "1", which may be to identify the number of matrix values which are not "0". In other words, because a matrix value which is not "0" in an irradiation time length matrix is a spot needed to irradiate radiation, when the number of matrix values which are not "0" becomes minimum, the number of radiation irradiation spots may become minimum. When the number of the radiation irradiation spots becomes minimum, because a time taken to change a location of a radiation source or change an irradiation direction becomes minimum except for a time taken to actually irradiate radiation and perform therapy, a time taken to perform overall therapy may become minimum.

As shown in FIG. 7, when comparing a case where the $L_1$-norm algorithm is applied with a case where the $L_0$-norm algorithm is applied, there is not much difference in the sum of all time lengths of irradiation, but the result where the number of radiation irradiation spots when the $L_0$-norm algorithm is applied is less than the number of radiation irradiation spots when the $L_1$-norm algorithm is applied may be derived. In other words, a time length where radiation is actually irradiated when the $L_1$-norm algorithm is applied is similar to a time length where radiation is actually irradiated when the $L_0$-norm algorithm is applied, but, as a time taken to move a radiation source or change an irradiation direction and the number of times of radiation irradiation are increased when the $L_0$-norm algorithm is applied, a time taken to unload the radiation source to the outside of the body and load it into the inside of the body again may be reduced. Thus, the entire therapy time may be reduced, and the amount of internal exposure to radiation, which is generated when the radiation source is unloaded and loaded, may also be reduced.

Furthermore, the condition where the dose for the area except for the target area becomes minimum may include a condition where a value, obtained by applying the $L_2$-norm algorithm to a difference between multiplication of the separate kernel matrix and the irradiation time length matrix for each group and an ideal voxel dose matrix for each group (e.g., a voxel dose matrix generated based on the result calculated by applying a dose distribution obtained when applying radiation intensity to be applied to real therapy in water in a specific direction to the Monte Carlo simulation method), becomes minimum. The ideal voxel dose matrix may be a matrix which includes a dose value, which should be provided to each voxel, as a matrix value with respect to a target area group and a matrix in which all matrix values are "0" with respect to a normal body area group. Thus, when the value obtained by applying the $L_2$-norm algorithm to the difference between the multiplication of the separate kernel matrix and the irradiation time length matrix for each group and the ideal voxel dose matrix for each group becomes minimum, a desired dose value (i.e., a target dose) may be approximated to the target area and the minimum dose may affect a normal body area.

Figure 8:
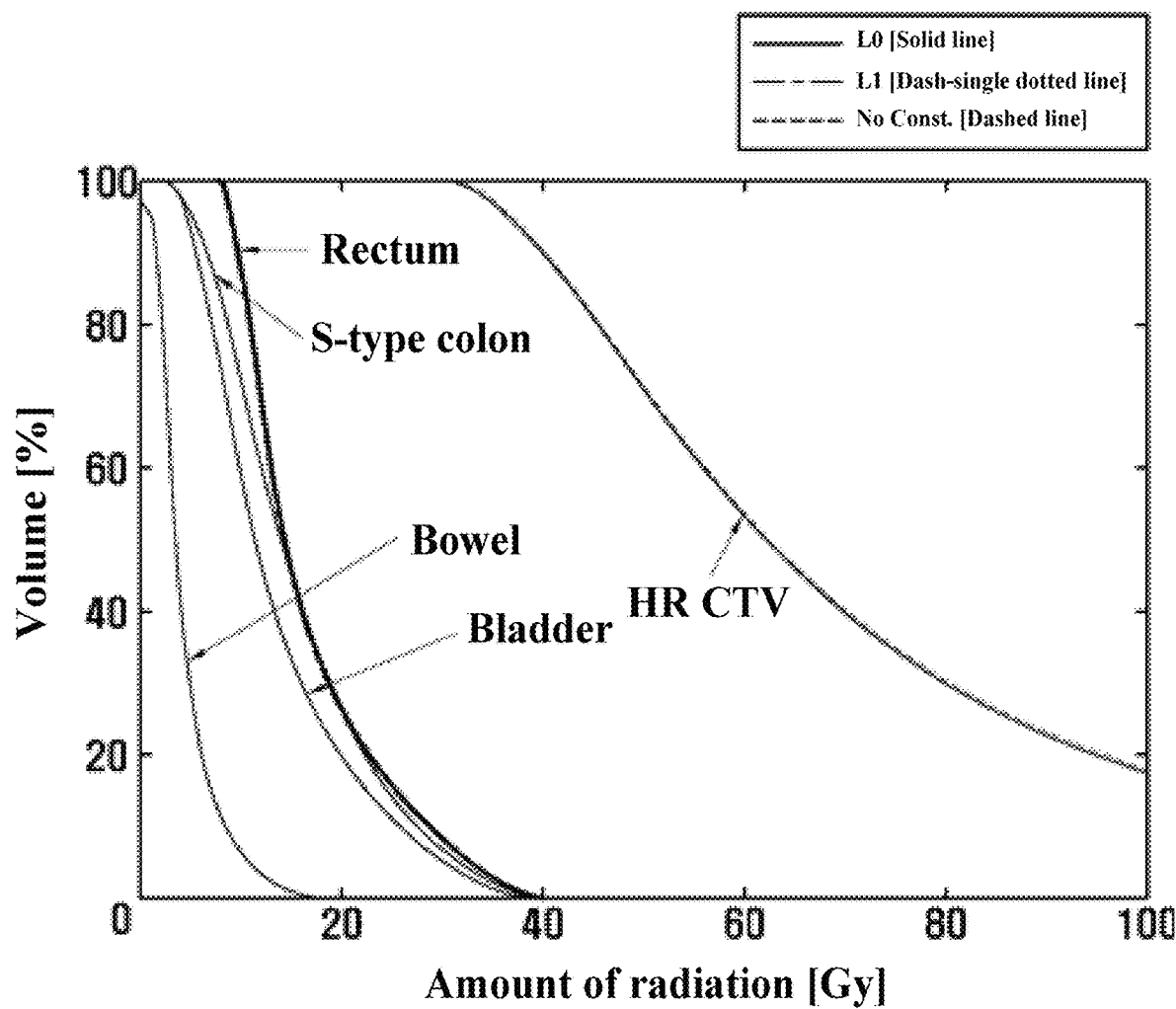
FIG. 8 is a drawing illustrating a dose volume histogram (DVH) of comparing therapy plans i) when not applying an $L_k$-norm algorithm, ii) when applying an $L_1$-norm algorithm, and iii) when applying an $L_0$-norm algorithm, according to an embodiment of the inventive concept.

Thus, to calculate a combination of time lengths of irradiation, which meets both of a condition (a first condition) where the number of radiation irradiation spots becomes minimum and ii) a condition where a dose for an area except for the target area becomes minimum, the computer may calculate a combination of time lengths of irradiation where a final calculation value, obtained by adding the sum of i) the result value obtained by applying the $L_0$-norm algorithm and ii) the value obtained by applying the $L_2$-norm algorithm to the difference between the multiplication of the separate kernel matrix for each group and the irradiation time length matrix for the group and the ideal voxel dose matrix for the group, becomes minimum among combinations of time lengths of irradiation. A formula where the computer calculates a combination of time lengths of irradiation, which meets the first condition and the second condition, based on matrix calculation is as follows:

$$\min_x \cdot \sum_{i=1}^{N} \alpha_i \|A_i x - d_i\|_2^2 + \lambda \|x\|_0 \quad \text{[Equation 1]}$$

di: ideal dose distribution for group i
Ai: separate kernel matrix for group i
αi: importance index for group i
λ: importance index for group i
x: time length of irradiation FIG. 8 is a drawing illustrating a dose volume histogram (DVH) of comparing therapy plans i) when not applying an $L_k$-norm algorithm, ii) when applying an $L_1$-norm algorithm, and iii) when applying an $L_0$-norm algorithm, according to an embodiment of the inventive concept.

FIG. 8 illustrates comparing therapy plans for each organ in case of three algorithms with respect to a specific patient, which indicates the therapy plan with a dashed line on the graph i) when not applying the $L_k$-norm algorithm, indicates the therapy plan with a dash-single dotted line on the graph ii) when applying the $L_1$-norm algorithm, and indicates the therapy plan with a solid line on the graph iii) when applying the $L_0$-norm algorithm.

Referring to FIG. 8, it may be verified that DVH curves drawn by the three algorithms are almost the same to the point of being unable to divide them per organ.

Thus, quality of the therapy plan when using the $L_0$-norm algorithm according to an embodiment of the inventive concept, which has less radiation irradiation spots, may be almost the same as quality of the therapy plan when applying the $L_1$-norm algorithm or quality of the therapy plan when not applying the $L_k$-norm algorithm.

As a result, the $L_0$-norm algorithm according to an embodiment of the inventive concept may reduce the entire therapy time while maintaining the quality of the therapy plan and may reduce the amount of exposure to radiation provided to the inside, which is generated when unloading and loading a radiation source, thus being more effective than the other algorithms.

Figure 9:
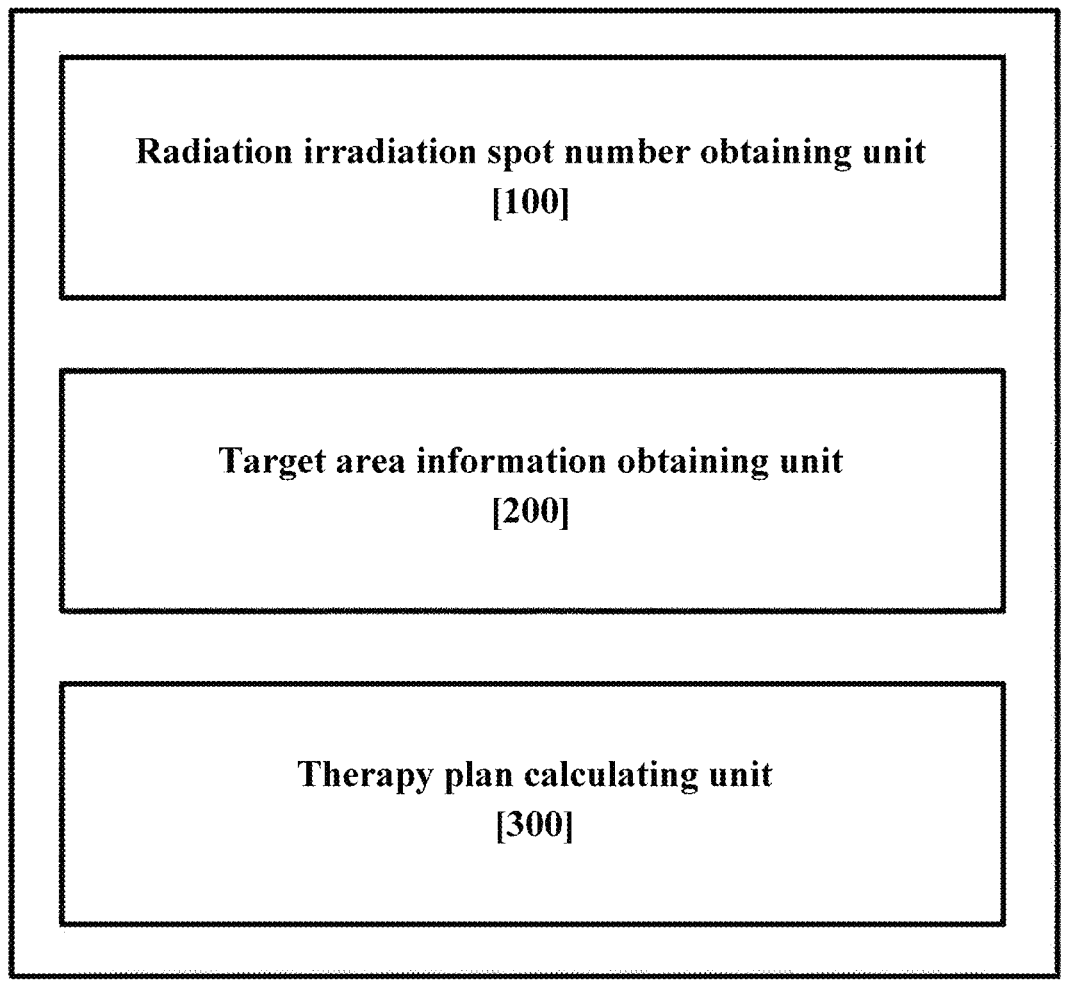
FIG. 9 is a block diagram illustrating an internal configuration of a device for calculating a brachytherapy plan according to another embodiment of the inventive concept.

FIG. 9 is a block diagram illustrating an internal configuration of a device for calculating a brachytherapy plan according to an embodiment of the inventive concept.

Referring to FIG. 9, the device for calculating the brachytherapy plan according to an embodiment of the inventive concept may include a radiation irradiation spot number obtaining unit 100, a target area information obtaining unit 200, and a therapy plan calculating unit 300. Hereinafter, contents previously described in conjunction with each component will be omitted.

The radiation irradiation spot number obtaining unit 100 may obtain the number of radiation irradiation spots based on radiation irradiation information. The radiation irradiation information may include the number of locations capable of arranging radiation sources and an angle change unit. The radiation irradiation spot may be a specific angle direction at a specific source location.

The target area information obtaining unit 200 may obtain target area information from a patient body model generated based on medical image data of a patient. The target area information may include arrangement information on a voxel space included in a target area.

The therapy plan calculating unit 300 may calculate radiation irradiation spots to which radiation is irradiated and a time length of irradiation to each of the radiation irradiation spots, based on the radiation irradiation information and the target area information.

Furthermore, as another embodiment, the therapy plan calculating unit 300 may calculate a combination of time lengths of irradiation to radiation irradiation spots, the number of which becomes minimum.

Furthermore, as another embodiment, the therapy plan calculating unit 300 may divide a target area and a plurality of body areas respectively corresponding to body tissues into a separate group, may generate a separate kernel matrix by setting the number of the radiation irradiation spots to a column number n and setting the number of voxels of each separate group to a row number m, may generate a voxel dose matrix, which is an m×1 matrix, by applying a characteristic value of a voxel included in each group to a matrix value in the separate kernel matrix depending on a specific rule and applying a dose value for each voxel to the same voxel order assignment rule as the kernel matrix to accomplish a radiation therapy effect, may generate an irradiation time length matrix, which is an n×1 matrix, for a time length of irradiation to each radiation irradiation spot, and may calculate a combination of time lengths of irradiation to each radiation irradiation spot where multiplication of the separate kernel matrix and the irradiation time length matrix, which correspond to each group, is approximated to the voxel dose matrix for each group. The separate kernel matrix may have the same column number by applying the same radiation irradiation spot condition.

Furthermore, as another embodiment, the therapy plan calculating unit 300 may extract a combination meeting a condition where the number of radiation irradiation spots becomes minimum and a condition where a dose for an area except for the target area becomes minimum, among combinations of time lengths of irradiation.

Figure 10:
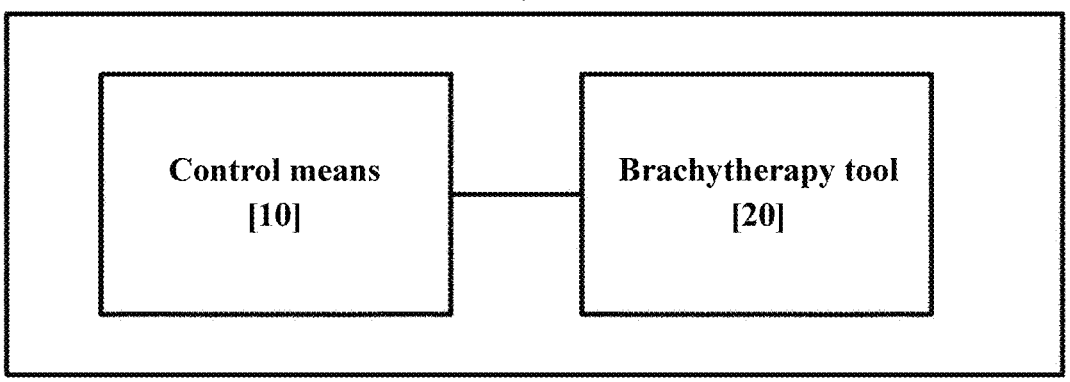
FIG. 10 is a block diagram illustrating a configuration of a brachytherapy apparatus according to another embodiment of the inventive concept.

FIG. 10 is a block diagram illustrating a configuration of a brachytherapy apparatus according to another embodiment of the inventive concept.

Referring to FIG. 10, a brachytherapy apparatus 1 according to another embodiment of the inventive concept may include a control means 10 and a brachytherapy tool 20. Hereinafter, contents described previously in conjunction with each component will be omitted.

The brachytherapy tool 20 may be inserted into the body to control a radiation irradiation direction and radiation irradiation intensity.

The control means 10 may obtain the number of radiation irradiation spots based on radiation irradiation information, may obtain target area information from a patient body model generated based on medical image data of a patient, may calculate radiation irradiation spots to which radiation is irradiated and a combination of time lengths of irradiation to each of the radiation irradiation spots, and may calculate a combination of time lengths of irradiation to radiation irradiation spots, the number of which becomes minimum, where a dose irradiated to a normal tissue becomes minimum. The radiation irradiation information may include the number of locations capable of arranging radiation sources and an angle change unit. The radiation irradiation spot may be a specific angle direction at a specific source location. The target area information may include arrangement information on a voxel space included in the target area.

The above-mentioned method for calculating a therapy plan according to an embodiment of the inventive concept may be implemented as a program (or application) to be combined with a computer which is hardware and be executed and may be stored in a medium.

For the computer to read the program and execute the methods implemented with the program, the above-mentioned program may include a code coded into a computer language such as C, C++, Java, or a machine language readable through a device interface of the computer by a processor (CPU) of the computer. Such a code may include a functional code associated with a function and the like defining functions necessary for executing the methods and may include a control code associated with an execution procedure necessary for the processor of the computer to execute the functions according to a procedure. Further, such a code may further include a code associated with memory reference about whether additional information or media necessary for the processor of the computer to execute the functions is referred at any location (address number) of an internal or external memory of the computer. Further, if it is necessary for the processor of the computer to communicate with any computer or server located in a remote place to execute the functions, the code may further include a communication related code about how communication is performed with any computer or server located in a remote place using a communication module of the computer and whether to transmit and receive any information or media upon communication.

The medium may refer to a device-readable medium which stores data on a semipermanent basis rather than a medium, such as a register, a cache, or a memory, which stores data during a short moment. The medium may refer to a device-readable medium which stores data on a semipermanent basis rather than a medium, such as a register, a cache, or a memory, which stores data during a short moment. In other words, the program may be stored in various storage media on various servers accessible by the computer or various storage media on the computer of the user. Further, the medium may be distributed to a computer system connected over a network and may store a computer-readable code on a distributed basis.

According to various embodiments of the inventive concept, there are the following various effects.

First, an embodiment of the inventive concept may optimize a brachytherapy plan to minimize a time taken to perform brachytherapy of a patient. In detail, an embodiment of the inventive concept may minimize the number of times that a brachytherapy tool is inserted into the body of the patient to prevent a therapy time from being increased according to an increase in the number of times that the brachytherapy tool is inserted into the body of the patient. In other words, an embodiment of the inventive concept may resolve inconvenience of the patient and time waste as the brachytherapy tool is inserted into the body of the patient many times in providing a target dose to a target area by the minimized number of times that the brachytherapy tool is inserted into the body of the patient. Furthermore, an embodiment of the inventive concept may minimize the number of times that a radiation source is moved and a change in radiation irradiation direction to minimize a time taken to treat the patient upon brachytherapy. An embodiment of the inventive concept may reduce a time taken to change a radiation irradiation location and direction of a radiation source and may reduce a time taken to unload the radiation source outside the body to supplement the radiation source and insert the radiation source into the body again, thus minimizing a brachytherapy time.

Secondly, an embodiment of the inventive concept may prevent an unnecessary dose from being provided to the body of the patient. In detail, an embodiment of the inventive concept may provide a dose similar to a target dose to a target area while minimizing a change in radiation irradiation location and a change in radiation irradiation direction and may minimize a dose affecting a normal body area. Furthermore, an embodiment of the inventive concept may minimize the number of times that the radiation source is moved, thus reducing the amount of exposure to radiation provided to the inside of the patient in the process of moving the radiation source.

While the inventive concept has been described with reference to exemplary embodiments, it will be apparent to those skilled in the art that various changes and modifications may be made without departing from the spirit and scope of the inventive concept. Therefore, it should be understood that the above embodiments are not limiting, but illustrative.

What is claimed is:

1. A method for calculating a brachytherapy plan using a therapy tool which is inserted into a body to control a radiation irradiation location and a radiation irradiation direction, the method comprising:
    obtaining, by a computer, the number of radiation irradiation spots based on radiation irradiation information, the radiation irradiation information including the number of locations capable of arranging radiation sources and an angle change unit and the radiation irradiation spot being a specific angle direction at a specific source location;
    obtaining, by the computer, target area information from a patient body model generated based on medical image data of a patient, the target area information including arrangement information on a voxel space included in a target area; and
    calculating, by the computer, radiation irradiation spots to which radiation is irradiated and a time length of irradiation to each of the radiation irradiation spots, based on the radiation irradiation information and the target area information,
    wherein the calculating includes:
    calculating a combination of time lengths of irradiation to radiation irradiation spots, the number of which becomes minimum, among combinations of time lengths of irradiation to a plurality of radiation irradiation spots for the target area.

2. The method of claim 1, wherein the calculating includes:
calculating the time length of irradiation to the radiation irradiation spot by applying the result, calculated by applying a dose distribution obtained when applying radiation intensity to be applied to rear therapy in water in a specific direction to the Monte Carlo simulation method, to each radiation irradiation spot in the patient body model.

3. The method of claim 2, further comprising:
moving a radiation irradiation location along a straight line in the direction of a specific axis,
wherein the calculating includes:
correcting and applying the result of Monte Carlo calculations depending on information tilted in the direction of the axis.

4. The method of claim 1, wherein the calculating includes:
generating a kernel matrix, which is an m×n matrix, by setting the number of the radiation irradiation spots to a column number n and setting the number of voxels of a specific group to a row number m;
applying a characteristic value of a voxel included in each group to a matrix value in the kernel matrix depending on a specific rule;
generating a voxel dose matrix, which is an m×1 matrix, by applying a dose value for each voxel to the same voxel order assignment rule as the kernel matrix to accomplish a radiation therapy effect;
generating an irradiation time length matrix, which is an n×1 matrix, for a time length of irradiation to each radiation irradiation spot; and
calculating a combination of time lengths of irradiation to each radiation irradiation spot where multiplication of the kernel matrix and the irradiation time length matrix, which correspond to the group, is approximated to the voxel dose matrix for the group.

5. The method of claim 4, further comprising:
dividing the target area and a plurality of body areas, each of which has a different characteristic, into a separate group.

6. The method of claim 5, wherein the generating of the kernel matrix includes:
generating a separate kernel matrix for each separate group,
wherein the calculating of the combination of the time lengths of irradiation includes:
calculating a radiation irradiation length combination meeting the separate kernel matrix for each separate group and the voxel dose matrix, and
wherein the separate kernel matrix has the same column number by applying the same radiation irradiation spot condition.

7. The method of claim 6, wherein the calculating further includes:
extracting a combination meeting a condition where the number of radiation irradiation spots becomes minimum and a condition where a dose for an area except for the target area becomes minimum, among combinations of time lengths of irradiation.

8. The method of claim 7, wherein the condition where the number of the radiation irradiation spots becomes minimum includes a condition where a value obtained by applying an $L_0$-norm algorithm becomes minimum, among the combinations of the time lengths of irradiation.

9. The method of claim 7, wherein the condition where the dose for the area except for the target area becomes minimum includes a condition where a value obtained by applying an $L_2$-norm algorithm to a difference between multiplication of the separate kernel matrix and the irradiation time length matrix for the group and an ideal voxel dose matrix for each group becomes minimum.

10. A non-transitory computer readable medium storing a computer program, and coupled with a computer hardware, for calculating a brachytherapy plan, wherein the program is configured to execute:
obtaining, by a computer, the number of radiation irradiation spots based on radiation irradiation information, the radiation irradiation information including the number of locations capable of arranging radiation sources and an angle change unit and the radiation irradiation spot being a specific angle direction at a specific source location;
obtaining, by the computer, target area information from a patient body model generated based on medical image data of a patient, the target area information including arrangement information on a voxel space included in a target area; and
calculating, by the computer, radiation irradiation spots to which radiation is irradiated and a time length of irradiation to each of the radiation irradiation spots, based on the radiation irradiation information and the target area information,
wherein the calculating includes:
calculating a combination of time lengths of irradiation to radiation irradiation spots, the number of which becomes minimum, among combinations of time lengths of irradiation to a plurality of radiation irradiation spots for the target area.

11. A device for calculating a brachytherapy plan using a therapy tool which is inserted into the body to control a radiation irradiation location and a radiation irradiation direction, the device comprising:
a radiation irradiation spot number obtaining unit configured to obtain the number of radiation irradiation spots based on radiation irradiation information;
a target area information obtaining unit configured to obtain target area information from a patient body model generated based on medical image data of a patient; and
a therapy plan calculating unit configured to calculate radiation irradiation spots to which radiation is irradiated and a time length of irradiation to each of the radiation irradiation spots, based on the radiation irradiation information and the target area information,
wherein the radiation irradiation information includes the number of locations capable of arranging radiation sources and an angle change unit,
wherein the radiation irradiation spot is a specific angle direction at a specific source location,
wherein the target area information includes arrangement information on a voxel space included in a target area, and
wherein the therapy plan calculating unit calculates a combination of time lengths of irradiation to radiation irradiation spots, the number of which becomes minimum, among combinations of time lengths of irradiation to a plurality of radiation irradiation spots for the target area.

12. The device of claim 11, wherein the therapy plan calculating unit calculates the time length of irradiation to the radiation irradiation spot by applying the result, calculated by applying a dose distribution obtained when applying radiation intensity to be applied to rear therapy in water in a specific direction to the Monte Carlo simulation method, to each radiation irradiation spot in the patient body model.

13. The device of claim 12, wherein an irradiation location of the radiation is moved along a straight line in the direction of a specific axis, wherein the therapy plan calculating unit corrects and applies the result of Monte Carlo calculations depending on information tilted in the direction of the axis.

14. The device of claim 11, wherein the therapy plan calculating unit is further configured to:

generate a kernel matrix, which is an m×n matrix, by setting the number of the radiation irradiation spots to a column number n and setting the number of voxels of a specific group to a row number m, apply a characteristic value of a voxel included in each group to a matrix value in the kernel matrix depending on a specific rule, generate a voxel dose matrix, which is an m×1 matrix, by applying a dose value for each voxel to the same voxel order assignment rule as the kernel matrix to accomplish a radiation therapy effect, generate an irradiation time length matrix, which is an n×1 matrix, for a time length of irradiation to each radiation irradiation spot, and calculate a combination of time lengths of irradiation to each radiation irradiation spot where multiplication of the kernel matrix and the irradiation time length matrix, which correspond to the group, is approximated to the voxel dose matrix for the group.

15. The device of claim 11, wherein the therapy plan calculating unit is further configured to:

divide the target area and a plurality of body areas respectively corresponding to body tissues into a separate group in the patient body model, generate a separate kernel matrix by setting the number of the radiation irradiation spots to a column number n and setting the number of voxels of a specific group to a row number m, apply a characteristic value of a voxel included in each group to a matrix value in the separate kernel matrix depending on a specific rule, generate a voxel dose matrix, which is an m×1 matrix, by applying a dose value for each voxel to the same voxel order assignment rule as the kernel matrix to accomplish a radiation therapy effect, generates an irradiation time length matrix, which is an n×1 matrix, for a time length of irradiation to each radiation irradiation spot, and calculate a combination of time lengths of irradiation to each radiation irradiation spot where multiplication of the separate kernel matrix and the irradiation time length matrix, which correspond to each group, is approximated to the voxel dose matrix for each group, and wherein the separate kernel matrix has the same column number by applying the same radiation irradiation spot condition.

16. The device of claim 15, wherein the therapy plan calculating unit extracts a combination meeting a condition where the number of radiation irradiation spots becomes minimum and a condition where a dose for an area except for the target area becomes minimum, among combinations of time lengths of irradiation.

17. The device of claim 16, wherein the condition where the number of the radiation irradiation spots becomes minimum includes a condition where a value obtained by applying an $L_0$-norm algorithm becomes minimum, among the combinations of the time lengths of irradiation.

18. The device of claim 16, wherein the condition where the dose for the area except for the target area becomes minimum includes a condition where a value obtained by applying an $L_2$-norm algorithm to a difference between multiplication of the separate kernel matrix and the irradiation time length matrix for the group and an ideal voxel dose matrix for each group becomes minimum.

* * * * *